(12) United States Patent
Struble

(10) Patent No.: US 7,146,214 B2
(45) Date of Patent: Dec. 5, 2006

(54) ANTI-TACHYCARDIA PACING BASED ON MULTI-SITE ELECTROGRAMS

(75) Inventor: Chester Struble, Eljsden (NL)

(73) Assignee: Medtronic, Inc., Minneapolis, MN (US)

(*) Notice: Subject to any disclaimer, the term of this patent is extended or adjusted under 35 U.S.C. 154(b) by 452 days.

(21) Appl. No.: 10/126,522

(22) Filed: Apr. 22, 2002

(65) Prior Publication Data

US 2003/0199932 A1   Oct. 23, 2003

(51) Int. Cl.
*A61N 1/368* (2006.01)

(52) U.S. Cl. .................... 607/14; 607/15; 600/518

(58) Field of Classification Search .............. 607/14, 607/15, 4, 9; 600/518
See application file for complete search history.

(56) References Cited

U.S. PATENT DOCUMENTS

| | | | |
|---|---|---|---|
| 3,937,226 A | 2/1976 | Funke | |
| 4,088,140 A | 5/1978 | Rockland et al. | |
| 4,316,472 A | 2/1982 | Mirowski et al. | |
| 4,354,497 A | 10/1982 | Kahn | |
| 4,375,817 A | 3/1983 | Engle et al. | |
| 4,379,459 A | 4/1983 | Stein | |
| 4,384,585 A | 5/1983 | Zipes | |
| 4,476,868 A | 10/1984 | Thompson | |
| 4,556,063 A | 12/1985 | Thompson | |
| 4,727,877 A | 3/1988 | Kallok | |
| 4,821,723 A | 4/1989 | Baker et al. | |
| 4,880,005 A | 11/1989 | Pless et al. | |
| 4,928,688 A | 5/1990 | Mover | |
| 4,949,719 A | 8/1990 | Pless et al. | |
| 4,953,551 A | 9/1990 | Mehra | |
| 5,117,824 A | 6/1992 | Keimel et al. | |
| 5,131,388 A | 7/1992 | Pless | |
| 5,144,949 A | 9/1992 | Olson et al. | |
| 5,163,427 A | 11/1992 | Keimel | |
| 5,181,511 A * | 1/1993 | Nickolls et al. | ............... 607/14 |
| 5,188,105 A | 2/1993 | Keimel | |
| 5,312,453 A | 5/1994 | Shelto et al. | |
| 5,314,430 A | 5/1994 | Bardy | |
| 5,354,316 A | 10/1994 | Keimel | |
| 5,545,186 A | 8/1996 | Olson et al. | |
| 5,620,468 A | 4/1997 | Mongeon et al. | |
| 5,674,251 A | 10/1997 | Combs et al. | |
| 5,683,426 A | 11/1997 | Mehra | |
| 5,720,768 A * | 2/1998 | Verboven-Nelissen | ......... 607/9 |
| 5,873,896 A | 2/1999 | Ideker | |
| 6,078,837 A | 6/2000 | Peterson et al. | |
| 6,308,095 B1 * | 10/2001 | Hsu et al. | .................... 600/518 |
| 6,654,639 B1 * | 11/2003 | Lu | ............... 607/17 |

* cited by examiner

*Primary Examiner*—Kennedy Schaetzle
(74) *Attorney, Agent, or Firm*—Paul H. McDowall; Michael C. Soldner; Girma Wolde-Michael

(57) ABSTRACT

In one embodiment, a method includes sensing depolarizations of a heart at a plurality of different locations, and determining a sequence of the sensed depolarizations. The method may further include identifying a tachycardia condition and stimulating the heart at the plurality of locations based on the determined sequence. For example, the method may be implemented by an implantable medical device in order to improve anti-tachycardia pacing (ATP).

47 Claims, 11 Drawing Sheets

ANTI-TACHYCARDIA PACING BASED ON MULTI-SITE ELECTROGRAMS

FIELD OF THE INVENTION

The invention relates to cardiac pacing systems and, more particularly, to multiple-lead cardiac pacing systems.

BACKGROUND

An arrhythmia is a disturbance in the normal rate, rhythm or conduction of the heartbeat. Arrhythmia may originate in an atrium or a ventricle. Atrial tachycardia (AT) and ventricular tachycardia (VT) (collectively referred to as tachycardia), are forms of arrhythmia in which the atria or ventricles contract at a high rate, e.g., 100 or more beats per minute. Atrial fibrillation (AF) and ventricular fibrillation (VF) (collectively referred to as fibrillation) are other forms of arrhythmia, characterized by a chaotic and turbulent activation of atrial or ventricle wall tissue. The number of depolarizations per minute during fibrillation can exceed 400. In addition, the fibrillation stimuli can occur in the refractory period of the surrounding myocardium.

Tachycardia can lead to fibrillation, which in turn can be life threatening. Tachycardia is also associated with other low cardiac output symptoms, such as fatigue. Many tachycardias are episodic, marked by abrupt onset but also abrupt termination. Still, tachycardia can cause considerable patient distress. Moreover, if untreated, tachycardia can lead to other dangerous life-threatening conditions, such as the development of blood clots which can cause stroke and possibly death.

Treatment for tachycardia may include anti-tachycardia pacing (ATP) or cardioversion, in which a train of high rate pulses or one or more high energy pulses is delivered to the heart in an attempt to restore a more normal rhythm. ATP is typically effective in converting stable tachycardias to normal sinus rhythm, and is often delivered via an implanted device. In many cases, a sequence of increasingly aggressive ATP therapies are applied until an episode of tachycardia is terminated. The implanted device can be configured to discontinue ATP and immediately apply cardioversion in the event the tachycardia degrades into fibrillation.

For some tachycardia episodes, existing ATP techniques may not be completely effective. For example, tachycardia may originate in a very localized site within a specific heart chamber. In that case, existing ATP techniques may apply therapy at locations or times that are not effective to end the tachycardia condition. Accordingly, there is a need for improved ATP therapy. Table 1 below lists a number of documents that disclose implantable devices designed to deliver ATP.

TABLE 1

| U.S. Pat. No. | Inventor | Issue Date |
| --- | --- | --- |
| 3,937,226 | Funke | Feb. 10, 1976 |
| 4,088,140 | Rockland et al. | May 09, 1978 |
| 5,683,429 | Mehra | Nov. 04, 1997 |
| 4,354,497 | Kahn | Oct. 19, 1982 |
| 4,928,688 | Mower | May 29, 1990 |
| 5,873,896 | Ideker | Feb. 23, 1999 |
| 6,078,837 | Peterson et al. | Jun. 20, 2000 |
| 5,620,468 | Mongeon et al. | Apr. 15, 1997 |
| 5,674,251 | Combs et al. | Oct. 07, 1997 |

All patents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to cardiac pacemakers in general, and ATP techniques in particular. These problems include, for example, a failure to appreciate and fully exploit the usefulness of information provided by multiple electrodes of a multi-site pacemaker. In particular, existing ATP techniques have not effectively harnessed information provided by multiple electrodes of a multi-site pacemaker to improve or optimize ATP therapy. Consequently, existing ATP techniques have been limited in their ability to identify episodic origins of tachycardia, and quickly terminate some tachycardia episodes. Various embodiments of the present invention have the object of solving at least one of the foregoing problems.

It is an object of the invention to improve ATP therapy techniques of an implantable device. Improved ATP therapy techniques can reduce the likelihood that the tachycardia will lead to more life-threatening problems such as fibrillation, blood clots, or stroke. In this light, it is an object of the invention to enhance the quality of life and prolong the life expectance of persons susceptible to tachycardia episodes.

It is a further object of the invention to effectively harness the information provided by multiple leads of a multi-site pacemaker to improve or optimize ATP therapy. In particular, multi-site pacemakers that employ a number of electrodes via multiple different leads may provide information that can be advantageously exploited to improve ATP therapy.

It is a further object of the invention to identify a sequence of tachycardia, and monitor its progression through a chamber or various chambers of the heart. Moreover, it is an object to of the invention to use the determined sequence to define a therapy sequence of pulses to be applied by an implantable medical device to more quickly and effectively terminate an episode of tachycardia.

It is a further object of the invention to determine a timing of the sequence. Moreover, it is an object to use the determined sequence and the timing of the sequence to define a timed sequence of therapeutic stimuli to be applied by an implantable medical device.

It is a further object of the invention to determine a period associated with the tachycardia. Moreover, it is an object to use the determined period to define a repolarization period associated with each site, during which time pulses can be applied at that site by an implantable medical device. In other words, the determined period can be used in conjunction with the detected sequence and timing to define a timed sequence of therapeutic stimuli to be applied by an implantable medical device.

It is a further object to identify a site of the heart that experiences the earliest onset of depolarization during a tachycardia episode. Moreover, it is an object to deliver therapeutic stimuli to the site that experiences the earliest onset of depolarization prior to delivering stimuli to other sites.

Various embodiments of the invention may possess one or more features capable of fulfilling the above objects. In general, the invention is directed to techniques of ATP therapy delivered via an implantable medical device. In one embodiment, the invention is directed to a method that includes sensing a plurality of different depolarizations of a heart at a plurality of different locations, and determining a sequence of the sensed depolarizations. The method may further include identifying a tachycardia condition and stimulating the heart at the locations based on the determined sequence. In other words, the sequence of stimulations applied to the heart may be the same as or similar to the determined sequence of sensed depolarizations.

For example, the invention may be embodied in an implantable medical device that carries out the described methods, a system within the device that executes the methods, a computer readable medium that stores instructions which can be executed by a device to carry out the methods, and other embodiments. In general, the invention may be implemented in hardware, software, firmware, or any combination thereof.

The invention may offer one or more advantages. For example, the invention may improve ATP therapy, and thereby improve the quality of life and life expectancy of patients that experience tachycardia episodes. The invention may achieve these advantages by exploiting sensed depolarizations of the heart in a multi-electrode setting. In other words, the invention can exploit a multi-electrode pacemaker setting to map episodes of tachycardia. The mapping can then be used to improve anti-tachycardia therapy specifically for the mapped episode. In this manner, the episode of tachycardia can be more effectively terminated by an episode specific delivery sequence of stimuli.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

In the following detailed description of the preferred embodiments, reference is made to the accompanying drawings that form a part hereof, and in which are shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
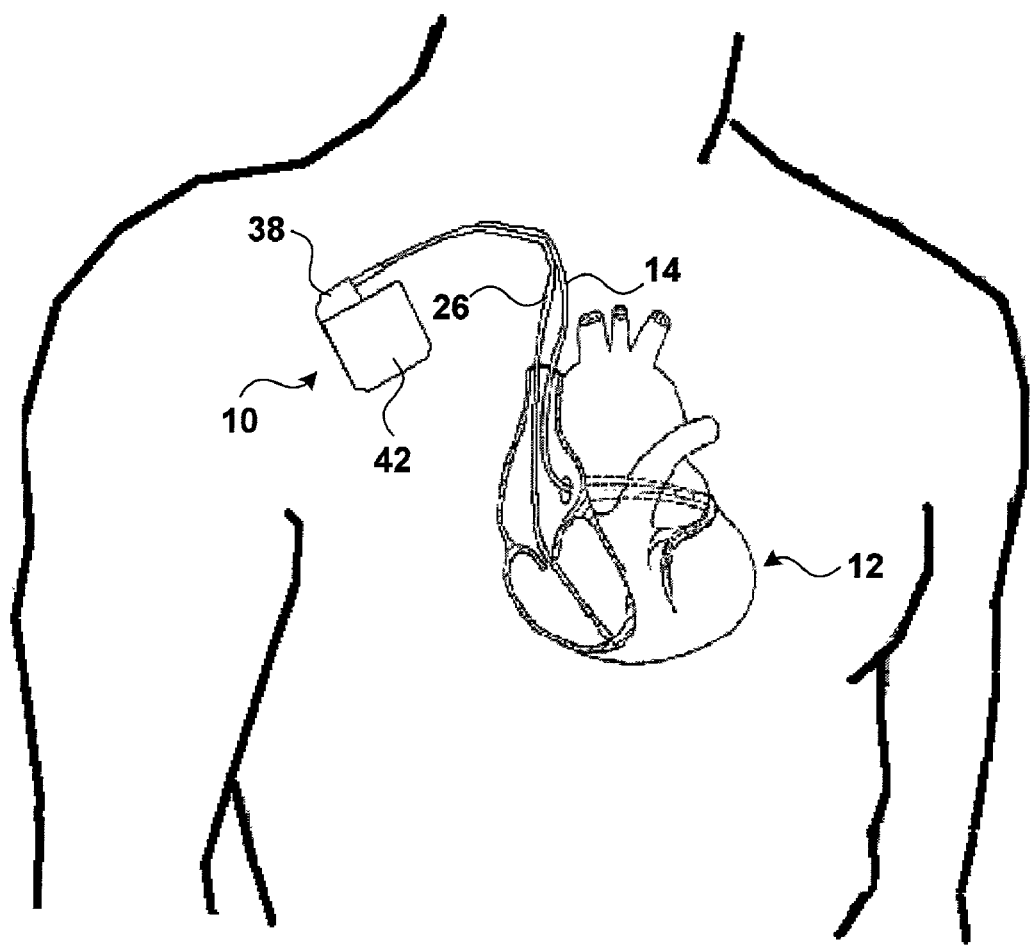
FIG. 1 is a schematic view of an exemplary implantable medical device within a human patient.

FIG. 1 is a simplified schematic view of pacemaker 10 within a patient's body. Pacemaker 10 represents one embodiment of an implantable medical device of the present invention. Pacemaker 10 shown in FIG. 1 comprises at least two pacing and sensing leads 14 and 26 attached to connector module 38 of hermetically sealed housing 42 and implanted near human or mammalian heart 12. Pacing and sensing leads 14 and 26 sense electrical signals attendant to the depolarization and repolarization of heart 12, and further provide pacing pulses for causing depolarization of cardiac tissue in the vicinity of the distal ends thereof. Leads 14 and 26 may have unipolar or bipolar electrodes disposed thereon, as is well known in the art. Although FIG. 1 illustrates leads being positioned in the ventricles, it is understood that the invention can be applied to any multi-lead pacemaker setting including bi-atrial pacemakers, bi-ventricular pacemakers, multi-ventricular pacemakers, and the like. In other words, leads 14 and 26 may be positioned in any two chambers of the heart, respectively, or even the same chamber, if desired.

Examples of pacemaker 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety. As outlined in greater detail below, pacemaker 10 may employ anti-tachycardia pacing (ATP) techniques that utilize information provided by sensing leads 14 and 26 to define timings and sequences of pacing therapies to be applied. In this manner, ATP techniques can be improved to more effectively treat episodes of tachycardia.

Figure 2:
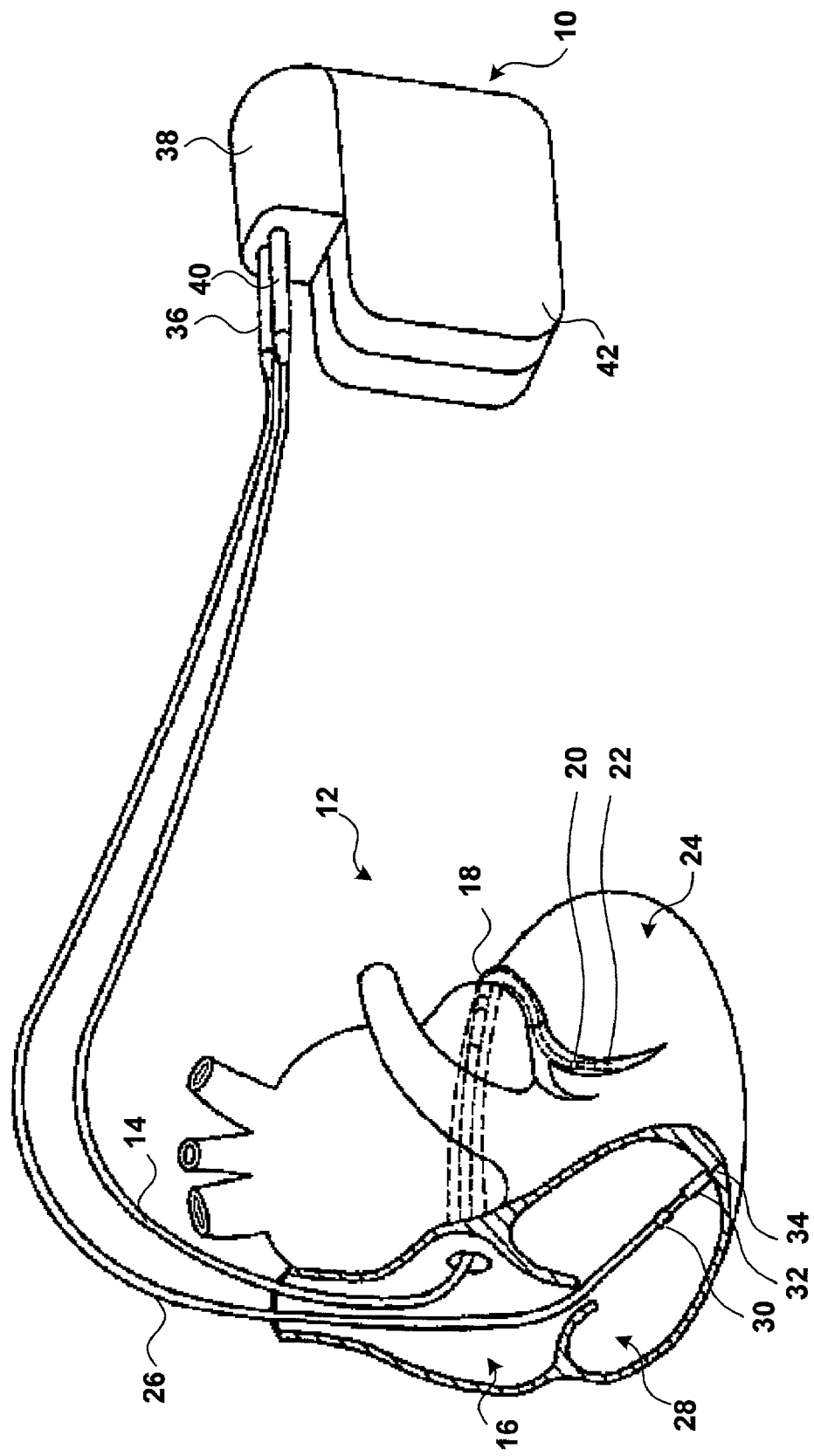
FIG. 2 is another schematic view an exemplary implantable medical device located in and near a heart.

FIG. 2 is a schematic representation of an exemplary implanted, two-channel cardiac pacemaker 10 in which the invention may be practiced. Pacemaker 10 is shown in conjunction with a human heart 12. Bipolar, endocardial left ventricular (LV) coronary sinus lead 14 is passed through a vein into the right atrium 16 of heart 12, into the coronary sinus 18 and then inferiorly in the great vein and cardiac veins extending from coronary sinus 18 to extend the distal ring pace/sense electrodes 20 and 22 alongside the LV chamber 24. The distal end of LV coronary sinus lead 14 positions ring electrodes 20 and 22 optimally with respect to the adjacent wall of left ventricle 24. Bipolar, endocardial right ventricular (RV) lead 26 is passed through the vein into right atrium 16 and into the right ventricle 28 where its distal ring and tip pace/sense electrodes 30 and 32 are fixed in place in the apex or in the interventricular septum by a distal attachment mechanism 34.

Pace/sense electrodes 20, 22, 30 and 32 sense electrical signals attendant to the depolarization and repolarization of heart 12. The electrical signals are conducted to pacemaker 10 via leads 14 and 26. Pace/sense electrodes 20, 22, 30 and 32 further deliver pacing pulses for causing depolarization of cardiac tissue in the vicinity of the distal ends thereof. The pacing pulses are generated by pacemaker 10 and are transmitted to pace/sense electrodes 20, 22, 30 and 32 via leads 14 and 26. In accordance with the invention, the pacing pulses generated by pacemaker 10 can be defined according to timing and sequence information determined by sensed electrical signals attendant to the depolarization and repolarization of heart 12. In particular, timing and sequence information can be determined from sense electrodes in order to determine where tachycardia is originating. Pacing pulses can then be defined according to the sensed timing and sequence information in order to treat the tachycardia. In that case, pacemaker 10 may include a control unit that generates the pacing pulses according to the timing and sequence information. The control unit, for example, may include a memory and a processor outlined below with reference to FIGS. 3 and/or 5.

RV lead 26 is formed with an in-line connector 36 fitting into a bipolar bore of pacemaker connector block 38. RV lead 26 includes a pair of electrically insulated conductors that couple distal tip pace/sense electrode 32 and proximal pace/sense ring electrode 30 to pacemaker 14. LV coronary sinus lead 14 is formed with an in-line connector 40 fitting into a bipolar bore of pacemaker connector block 38. LV coronary sinus lead 14 couples distal ring pace/sense electrode 22 and proximal pace/sense ring electrode 20 to pacemaker 14.

The pacing systems shown in FIGS. 1 and 2 are exemplary. In addition, the invention is not limited to the electrode placements shown in FIGS. 1 and 2. LV pace/sense electrodes 20 and 22, for example, may be located at a site other than coronary sinus 18. Both LV pace/sense electrodes 20 and 22 and RV pace/sense electrodes 30 and 32 may be epicardial, rather than endocardial as shown in FIG. 2. The pacing system may also include alternate or additional leads that deploy electrodes proximal to the atria for sensing or pacing. Indeed, as outlined in greater detail below, the effective deployment of additional sensing/pacing leads may improve ATP therapy in accordance with the invention. In some examples, multiple electrodes are disposed for sensing and pacing multiple locations of the various heart chambers. In other words, each chamber may include a number of electrodes for pacing and sensing.

Furthermore, the invention is not necessarily limited to the bipolar ventricular lead systems depicted in FIG. 2. The invention may be employed with unipolar lead systems that employ a single pace/sense electrode in the depicted positions proximal to right ventricle 24 and left ventricle 28, as well as other locations. Unipolar electrodes may cooperate with a remote electrode formed as part of the outer surface of the hermetically sealed housing 42 of pacemaker 10.

Figure 3:
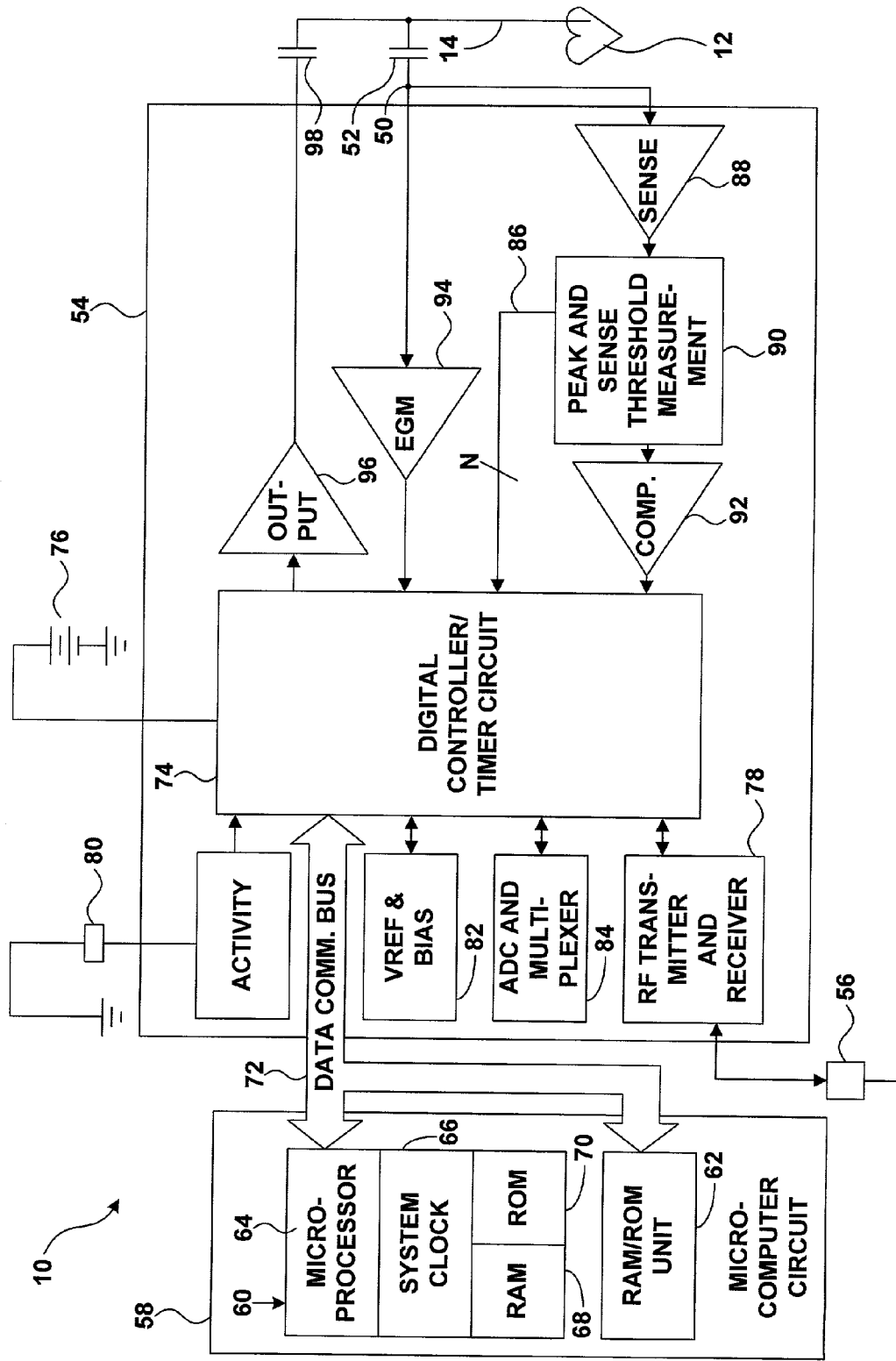
FIG. 3 is a block diagram illustrating constituent components of an implantable medical device as shown in FIGS. 1 and 2.

FIG. 3 shows a block diagram illustrating the constituent components of pacemaker 10 in accordance with one embodiment of the present invention. Pacemaker 10 is a pacemaker having a microprocessor-based architecture. Pacemaker 10 is shown as including activity sensor or accelerometer 80, which is preferably a piezoceramic accelerometer bonded to a hybrid circuit located inside housing 42 (shown in FIGS. 1 and 2). Activity sensor 80 typically (although not necessarily) provides a sensor output to activity circuitry 81 that varies as a function of a measured parameter relating to a patient's metabolic requirements. Activity circuitry 81 may condition the signal, such as by filtering or analog-to-digital conversion, before forwarding the signal to digital controller 74. For the sake of convenience, pacemaker 10 in FIG. 3 is shown with lead 14 only connected thereto. However, it is understood that similar circuitry and connections not explicitly shown in FIG. 3 apply to lead 26 (shown in FIGS. 1 and 2).

Pacemaker 10 in FIG. 3 is most preferably programmable by means of an external programming unit (not shown in the figures). One such programmer is the commercially available Medtronic Model 9790 programmer, which is microprocessor-based and provides a series of encoded signals to pacemaker 10, typically through a programming head which transmits or telemeters radio-frequency (RF) encoded signals to pacemaker 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker. In this manner, pacemaker 10 can be programmed to perform one or more of the pacing and sensing techniques outlined in greater detail below in order to more effectively treat tachycardia.

As shown in FIG. 3, lead 14 is coupled to node 50 in pacemaker 10 through input capacitor 52. Activity sensor or accelerometer 80 is most preferably attached to a hybrid circuit located inside hermetically sealed housing 42 of pacemaker 10. The output signal provided by activity sensor 80 is coupled to input/output circuit 54. Input/output circuit 54 contains analog circuits for interfacing with heart 12, activity sensor 80, antenna 56 and circuits for the application of stimulating pulses to heart 12. The rate of heart 12 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board random access memory (RAM) 68 and read-only memory (ROM) 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components. In some embodiments, the techniques for anti-tachycardia pacing described herein may be embodied in software stored on a computer readable medium such as RAM 68, ROM 70, or RAM/ROM unit of off-board circuit 62. In that case, the invention may be directed to the medium comprising computer readable instructions that perform the anti-tachycardia pacing techniques described herein. In still other embodiments, the invention may be directed toward a system that includes a processor, such as microprocessor 64 and memory such as on board RAM 68. In that case, RAM 68 may store instructions which microprocessor 64 executes to perform the anti-tachycardia pacing techniques described herein. In still other embodiments, the invention may be directed to an implantable medical device that includes electrodes coupled to a control unit. For example, the control unit may correspond to one or more components of FIG. 3, such as digital controller 74 and possibly other elements such as microcomputer 58.

Electrical components shown in FIG. 3 are powered by an appropriate implantable battery power source 76 in accordance with common practice in the art. For the sake of clarity, the coupling of battery power to the various components of pacemaker 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the selected programming and telemetry scheme permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of pacemaker 10 are coupled from microprocessor 64 via data bus 72 to digital controller/timer circuit 74, where digital timers and counters establish the overall escape interval of the pacemaker 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 14. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 86 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety. Further, digital controller/timer circuit 74 can be programmed to execute the anti-tachycardia pacing techniques described herein.

The electrogram signal provided by EGM amplifier 94 is employed when pacemaker 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 12 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 12. In some embodiments of the present invention, pacemaker 10 may operate in various non-rate-responsive modes. In other embodiments of the present invention pacemaker 10 may operate in various rate-responsive modes. Some embodiments of the present invention may be capable of operating in both non-rate-responsive and rate-responsive modes. Moreover, in various embodiments of the present invention pacemaker 10 may be programmably configured to operate so that it varies the rate at which it delivers stimulating pulses to heart 12 in response to one or more selected sensor outputs being generated. Numerous pacemaker features and functions not explicitly mentioned herein may be incorporated into pacemaker 10 while remaining within the scope of the present invention. In any case, pacemaker 10 executes anti-tachycardia pacing techniques in order to improve anti-tachycardia therapy in a multi-lead setting.

The present invention is not limited in scope to any particular number of sensors, and is not limited to pacemakers comprising activity or pressure sensors only. Although the present invention is useful in multiple-chamber pacemakers having two-sensors per lead, any number of sensors per lead may be employed. In other words, at least some embodiments of the present invention may be applied equally well in the contexts of single-, dual-, triple- or quadruple-chamber pacemakers or other types of pacemakers. See, for example, U.S. Pat. No. 5,800,465 to Thompson et al., hereby incorporated by reference herein in its entirety, as are all U.S. patents referenced therein.

Pacemaker 10 may also be a pacemaker combined with a cardioverter and/or defibrillator. Various embodiments of the present invention may be practiced in conjunction with a pacemaker-cardioverter-defibrillator such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
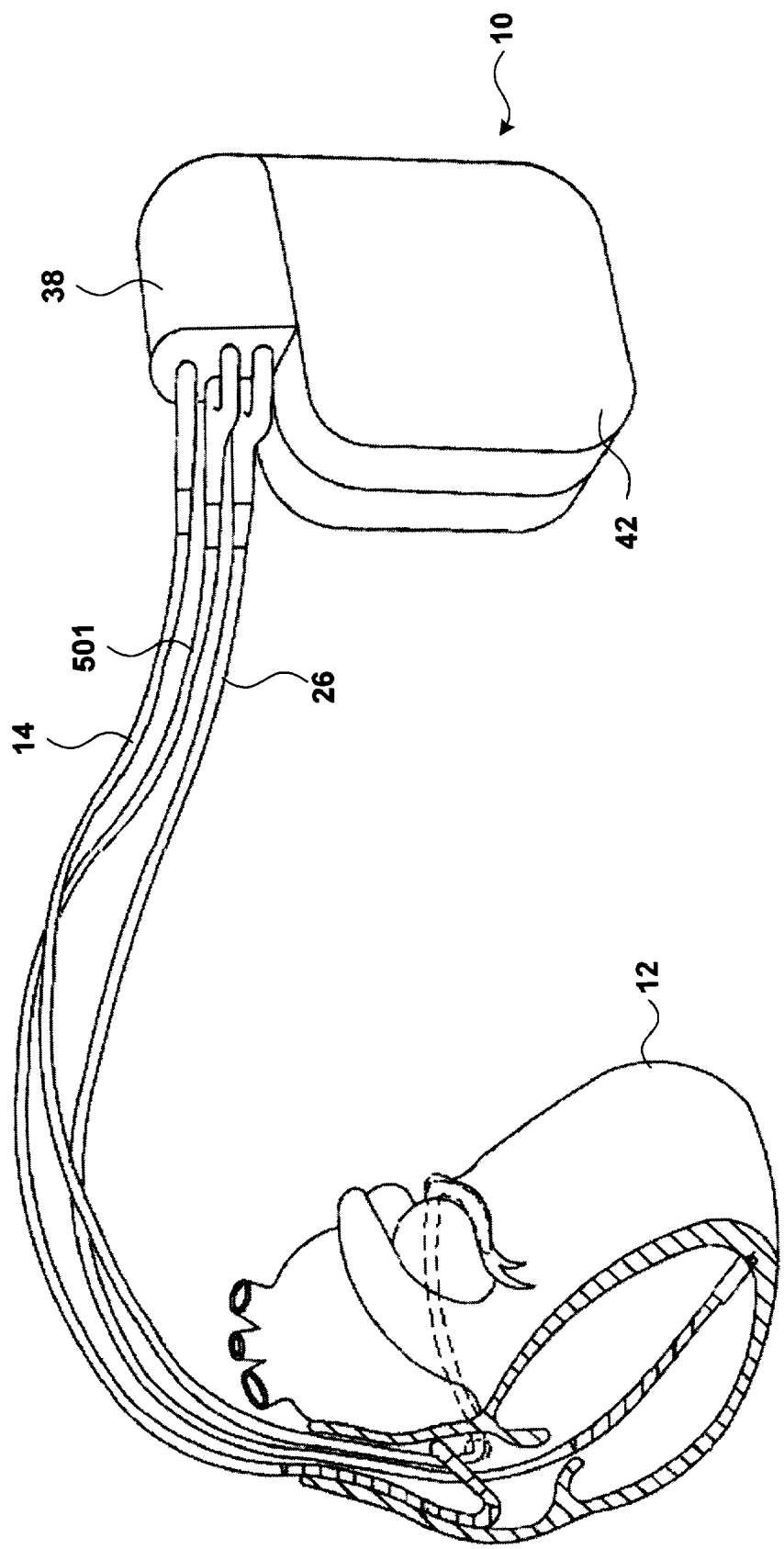
FIG. 4 is another schematic view an exemplary implantable medical device located in and near a heart.

FIG. 4 is another schematic representation of an exemplary implanted cardiac pacemaker 10 in which the invention may be practiced. In FIG. 4, pacemaker 10 is a three channel cardiac pacemaker shown in conjunction with a human heart 12. Left ventricular (LV) coronary sinus lead 14 is passed through a vein into the right atrium of heart 12, into the coronary sinus and then inferiorly in the great vein and cardiac veins extending from coronary sinus to extend the distal ring pace/sense electrodes alongside the LV chamber. The distal end of LV coronary sinus lead 14 positions ring electrodes optimally with respect to the adjacent wall of the left ventricle. Right ventricular (RV) lead 26 is passed through the vein into right atrium and into the right ventricle where its distal ring and tip pace/sense electrodes are fixed in place in the apex or in the interventricular septum. Right atrium (RA) lead 501 is positioned within the RA chamber, with distal end of RA lead 501 positioning ring electrodes optimally with respect to the adjacent wall of the right atrium or positioned within the atrial appendage.

As mentioned above, additional leads may also be used, and in some cases, may improve the effectiveness of anti-tachycardia pacing (ATP) techniques outlined in greater detail below. In any case, pacemaker 10 can be configured to provide ATP based on multi-site electrograms (EGMs). In particular, multiple signals received from the multiple electrodes can be used to map tachycardia. For example, the sequence and timing of depolarizations within the heart can be determined based on signals received from the multiple electrodes. The detected sequence and timing may then be used to define a sequence and timing for therapeutic stimuli to be provided to the heart. In this manner, ATP therapy can be improved. For example, by providing therapeutic stimuli to specific sites associated with the electrodes in a timed delivery sequence defined by the timing and sequence of detected depolarizations, specific episodes of tachycardia can be more quickly and reliably terminated.

Figure 5:
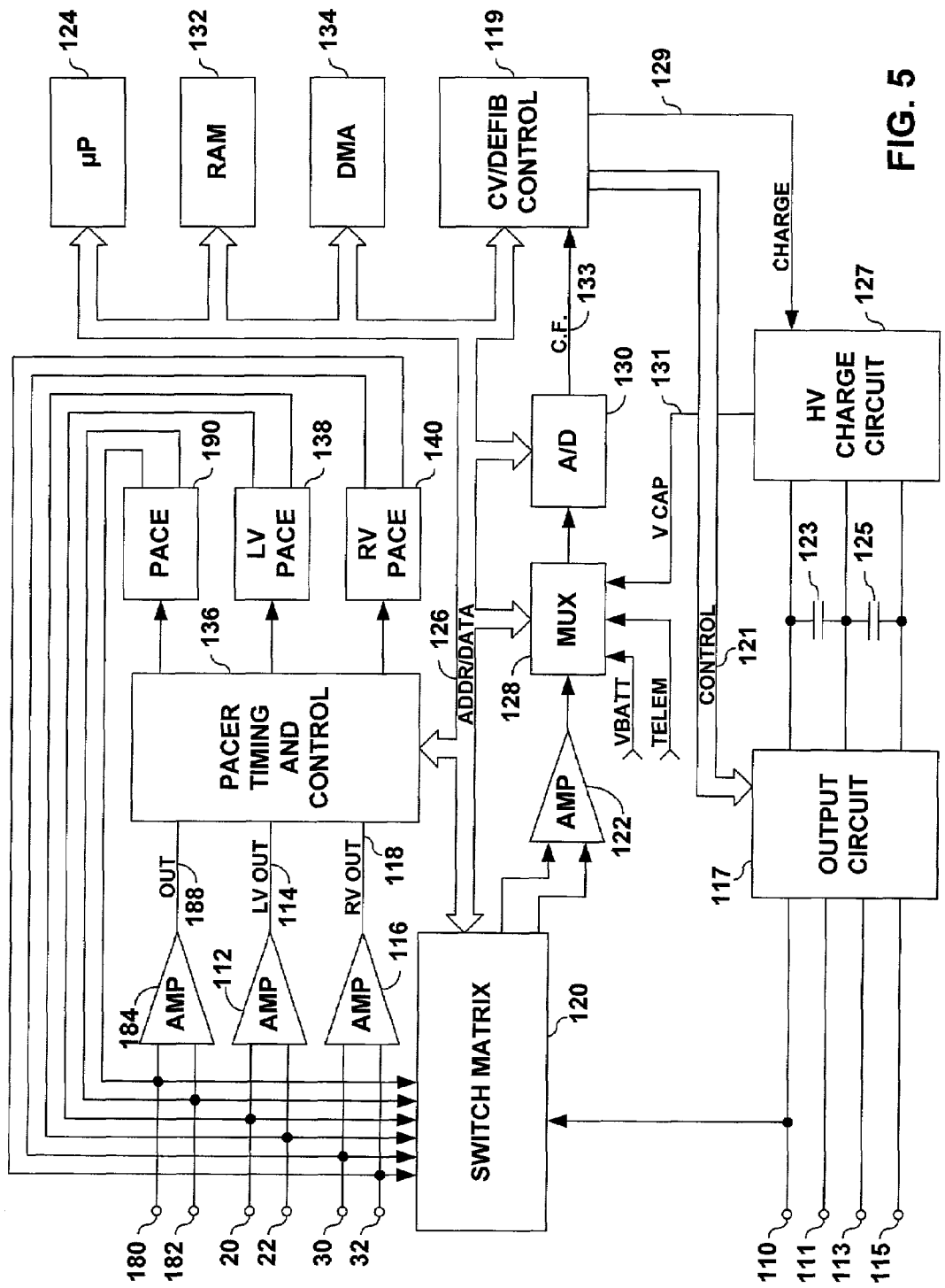
FIG. 5 is a functional block diagram of an exemplary embodiment of an implantable medical device as shown in FIG. 4.

FIG. 5 is a functional block diagram of an embodiment of pacemaker 10, such as that shown in FIG. 4 in which the pacemaker includes both pacing and defibrillation functionality. This diagram should be taken as exemplary of the type of device in which various embodiments of the present invention may be embodied, and not as limiting, as it is believed that the invention may be practiced in a wide variety of device implementations, including devices that provide anti-tachycardia pacing therapies but do not provide cardioverter and/or defibrillator functionality.

As shown in FIG. 5, pacemaker 10 is provided with an electrode system. Electrode 110 in FIG. 5 includes the uninsulated portion of housing 42 of pacemaker 10. Electrodes 110, 111, 113 and 115 are coupled to high voltage output circuit 117, which includes high voltage switches controlled by CV/defib control logic 119 via control bus 121. Switches disposed within circuit 117 determine which electrodes are employed and which electrodes are coupled to the positive and negative terminals of the capacitor bank (which includes capacitors 123 and 125) during delivery of defibrillation pulses.

Electrodes 20 and 22 are located on or in left ventricle 24 of the patient and are coupled to amplifier 112, which preferably takes the form of an automatic gain controlled amplifier providing an adjustable sensing threshold as a function of the measured R-wave amplitude. For example, electrodes 20 and 22 may be positioned proximate to distal end left ventricular (LV) coronary sinus lead 14 (FIG. 4). A signal is generated on LV out line 114 whenever the signal sensed between electrodes 20 and 22 exceeds the present sensing threshold.

Electrodes 30 and 32 are located on or in right ventricle 28 of the patient and are coupled to amplifier 116, which preferably also takes the form of an automatic gain controlled amplifier providing an adjustable sensing threshold as a function of the measured R-wave amplitude. For example, electrodes 30 and 32 may be positioned proximate to distal end of right ventricular (RV) lead 26 (FIG. 4). A signal is generated on RV out line 118 whenever the signal sensed between electrodes 30 and 32 exceeds the present sensing threshold. The general operation of amplifiers 112 and 116 may correspond to that disclosed in U.S. Pat. No. 5,117,824 to Keimel et al., hereby incorporated by reference herein in its entirety.

Electrodes 180 and 182 conceptually represent electrodes located at any desired location within or in proximity to heart 12. In one example, electrodes 180 and 182 may be positioned proximate to distal end of right atrium (RA) lead 501 (FIG. 4). However, in other embodiments, electrodes 180 and 182 may correspond to any other desired location. In many multi-site embodiments, pairs of electrodes are provided at a number of locations. For example, each atrium and each ventricle may have a pair of electrodes or a number of pairs for each chamber. In one specific example described in greater detail below, each atrium includes a pair of electrodes and four different pairs of electrodes are positioned within one or both of the ventricles. In other embodiments, a number of pairs of electrodes may be used specifically for one chamber of the heart. In general, however, any number of pairs of electrodes may be deployed in a variety of locations around the heart. Indeed, the techniques described herein may become more effective in treating tachycardia as more and more electrodes are deployed because a more complete mapping can be obtained, and a more precise therapy sequence can be delivered.

Switch matrix 120 is used to select which of the available electrodes are coupled to wide band (0.5–200 Hz) amplifier 122 for use in digital signal analysis. Selection of electrodes is controlled by microprocessor 124 via data/address bus 126, and the selections may be varied as desired. Signals from the electrodes selected for coupling to band pass amplifier 122 are provided to multiplexer 128, and thereafter converted to multi-bit digital signals by A/D converter 130, for storage in random access memory 132 under control of direct memory access circuit 134. Microprocessor 124 may employ digital signal analysis techniques to characterize the digitized signals stored in random access memory 132 to recognize and classify the patient's heart rhythm. Moreover, microprocessor 124 may execute ATP techniques outlined herein in order to improve the application of ATP therapy in a multi-lead pacemaker setting.

The remainder of the circuitry may be dedicated to the provision of cardiac pacing, cardioversion and defibrillation therapies in accordance with one or more embodiments of the invention. The following exemplary apparatus is disclosed for accomplishing pacing, cardioversion and defibrillation functions. Pacer timing/control circuitry 136 preferably includes programmable digital counters which control the basic time intervals associated with modes of pacing. Circuitry 136 also preferably controls escape intervals associated with pacing. In the exemplary bi-ventricular pacing environment, pacer timing/control circuitry 136 controls the ventricular escape interval that is used to time pacing pulses delivered to the ventricles.

Intervals defined by pacing circuitry 136 may also include atrial pacing escape intervals, the refractory periods during which sensed P-waves and R-waves are ineffective to restart timing of the escape intervals and the pulse widths of the pacing pulses. The durations of these intervals are determined by microprocessor 124, in response to stored data in memory 132 and are communicated to pacing circuitry 136 via address/data bus 126. Pacer circuitry 136 also determines the amplitude of the cardiac pacing pulses under control of microprocessor 124.

During pacing, escape interval counters within pacer timing/control circuitry 136 may be reset upon sensing of R-waves as indicated by a signals on lines 114 and 118. In accordance with the selected mode of pacing, pacer timing/control circuitry 136 triggers generation of pacing pulses by pacer output circuitry 138, 140 and 190 which are coupled to electrodes 20, 22, 30, 32 180 and 182. Escape interval counters may also be reset on generation of pacing pulses and thereby control the basic timing of cardiac pacing functions. The durations of the intervals defined by escape interval timers are determined by microprocessor 124 via data/address bus 126. The value of the count present in the escape interval counters when reset by sensed R-waves may be used to measure the durations of parameters such as R-R intervals, which measurements are stored in memory 132.

Microprocessor 124 most preferably operates as an interrupt driven device, and is responsive to interrupts from pacer timing/control circuitry 136 corresponding to the occurrence of sensed R-waves and corresponding to the generation of cardiac pacing pulses. Those interrupts are provided via data/address bus 126. Any necessary mathematical calculations to be performed by microprocessor 124 and any updating of the values or intervals controlled by pacer timing/control circuitry 136 take place following such interrupts.

In the event that generation of a cardioversion or defibrillation pulse is required, microprocessor 124 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 124 activates cardioversion/defibrillation control circuitry 119, which initiates charging of the high voltage capacitors 123 and 125 via charging circuit 127, under the control of high voltage charging control line 129. The voltage on the high voltage capacitors 123 and 125 is monitored via VCAP line 131, which is passed through multiplexer 128 and in response to reaching a predetermined value set by microprocessor 124, results in generation of a logic signal on Cap Full (CF) line 133 to terminate charging. Thereafter, timing of the delivery of the defibrillation or cardioversion pulse is controlled by pacer timing/control circuitry 136. Following delivery of the fibrillation or tachycardia therapy microprocessor 124 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 117 under the control of control circuitry 119 via control bus 121. Output circuit 117 determines whether a monophasic or biphasic pulse is delivered, the polarity of the electrodes and which electrodes are involved in delivery of the pulse. Output circuit 117 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the U.S. Pat. No. 4,953,551 to Mehra et al. and in U.S. Pat. No. 4,727,877 to Kallok, hereby incorporated by reference herein in their entireties.

An example of circuitry that may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

The embodiment shown in FIG. 5 is merely exemplary, and is intended to provide additional details pertaining to the exemplary embodiment shown in FIG. 4. The embodiment shown in FIG. 5 may be modified to include additional features, or may be adapted to other embodiments. For example, the embodiment in FIG. 5 may be modified for an implanted medical device having electrodes mounted on any number of leads not shown in FIG. 4, or may not include one or more of the leads shown in FIG. 4. Such electrodes may be coupled to a P-wave amplifier (not shown in FIG. 5) that, like amplifiers 112 an 116, provides an adjustable sensing threshold as a function of a measured P-wave amplitude. The embodiment shown in FIG. 5 may further be modified to detect activity in or near the left atrium of the patient.

In general, amplifier 184 is illustrated as being coupled to electrodes 180 and 182, which represent conceptually, electrodes attached to a lead positioned in any desired location. A signal is generated on out line 188 whenever the signal sensed between electrodes 180 and 182 exceeds a sensing threshold. Pacer timing/control circuitry 136 triggers generation of pacing pulses by pacer output circuitry 190, which is coupled to electrodes 180 and 182. In general, the invention may be adapted to include any number of electrodes, and thus any number of amplifiers that provide signals to timing and controlling circuitry 136. Any number of pacing output circuitries may also be employed to generate pacing pulses to the respective electrodes. Indeed, as outlined in greater detail below, as more electrodes are employed, the timing and periodic generation of pacing signals can be employed in a manner that may improve the effectiveness of anti-tachycardia pacing (ATP).

Microprocessor 124 may perform mathematical calculations to carry out tachycardia detection and therapy algorithms outlined in greater detail below. The present invention is believed to find wide application to any form of implantable electrical device for use in conjunction with electrical leads. In general some embodiments may be directed toward an implantable medical device that includes electrodes coupled to a control unit. With respect to FIG. 5, the control unit may include some but not necessarily all of the illustrated components. For example, in one embodiment, the control unit capable of executing the methods described below may include pacing and timing control 136, processor 124 and RAM 132, although additional components may also be included.

Figure 6:
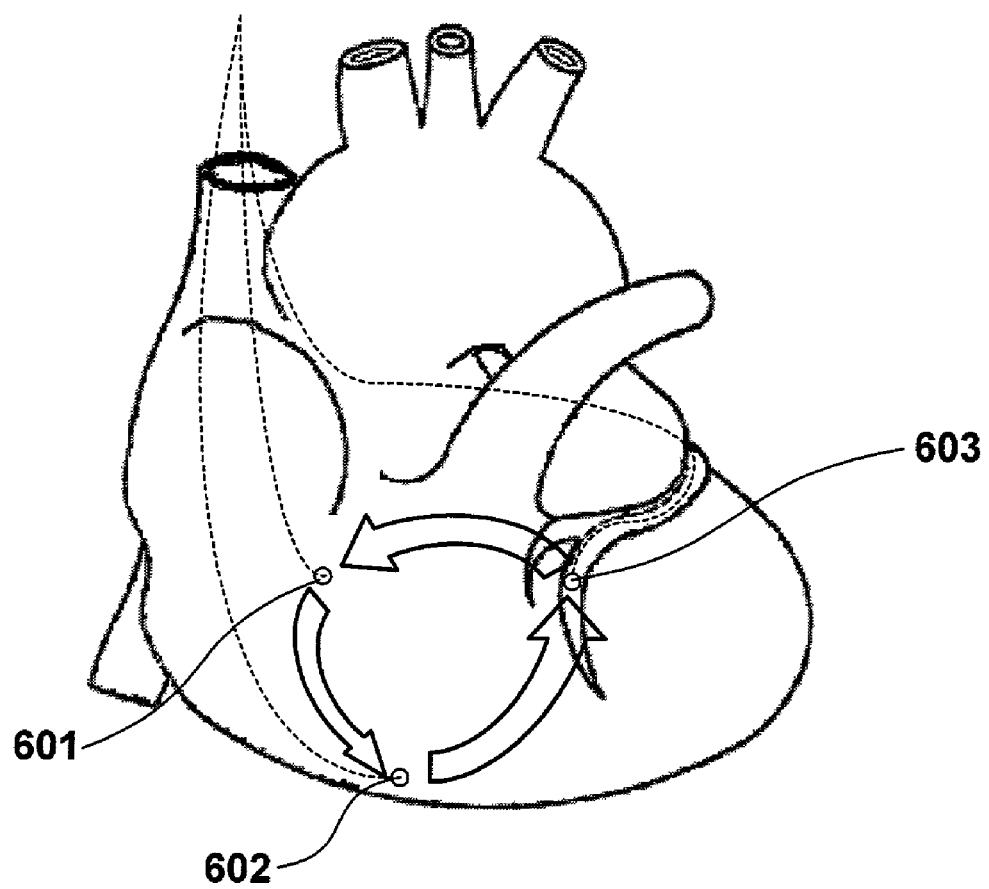
FIG. 6 is a schematic view of a heart and electrodes of an implantable medical device used to provide multi-site anti-tachycardia therapy to the heart.

FIG. 6 is a schematic view of a heart 12 as well as sense/pace electrodes 601, 602 and 603 of an implantable medical device used to provide anti-tachycardia therapy to the heart. For example, the implantable medical device may comprise a pacemaker, such as a pacemaker that includes the various functionality outlined above.

In accordance with the invention, anti-tachycardia pacing can be improved by exploiting sensed depolarizations of heart 12 in the multi-lead pacemaker setting. In particular, because tachycardia can originate in a relatively localized manner, and then spread throughout the heart chambers, multi-lead pacemakers that include multiple electrodes positioned around the heart for monitoring purposes may be used to provide a mapping of the tachycardia. Depolarizations of the heart during a tachycardia episode may occur according to a timed sequence. Thus, by detecting the sequence of depolarizations between different sites within the heart and a timing of the sequence, a spatial and temporal mapping of the tachycardia can be generated. Then, ATP therapy can be provided based on the mapping. For example, heart 12 can be stimulated according to a same or similar timed sequence to that of the detected depolarizations associated with the tachycardia, improving the likelihood of terminating the tachycardia and thereby restoring the heart to a normal sinus rhythm.

For example, as shown by the arrows in FIG. 6, tachycardia may begin at a localized site, such as a location in proximity to electrode 601. In that case, electrode 601 may be the first electrode to detect a depolarization of heart 12 during a tachycardia episode. In other words, electrode 601 may detect the earliest onset of depolarization. Shortly thereafter, electrode 602 may detect a depolarization, followed by electrode 603. In accordance with the invention, a sequence of depolarizations can be determined in order to provide a mapping of the tachycardia as the depolarizations move through one or more chambers of heart 12.

Moreover, the time between successively sensed depolarizations can be recorded to define a timing of the sequence. Then, ATP pacing therapies can be delivered to one or more chambers of heart 12 according to a timed sequence that is the same as or similar to the timed sequence of detected depolarizations. The stimuli can be delivered to heart 12 at optimal times for each site associated with the electrodes. In this manner, ATP therapy can be improved, particularly in an implantable medical device setting.

In addition to mapping the sequence of depolarizations, a period associated with the depolarizations may also be determined. For example, the time offset between successive depolarizations at a particular site associated with one or all of electrodes 601, 602 and 603 may be used to define a period of the tachycardia. In other words, the period between successive depolarizations at any given site may be used to define the period of the tachycardia episode. This determined period can then be used in conjunction with the detected sequence and timing to define windows of time when therapeutic stimuli can be provided at each site. The windows, for example, may defined repolarization periods for each site, during which a stimulus can be delivered. In this manner, therapeutic stimuli can be provided to heart 12 in order to restore normal sinus rhythm.

Figure 7:
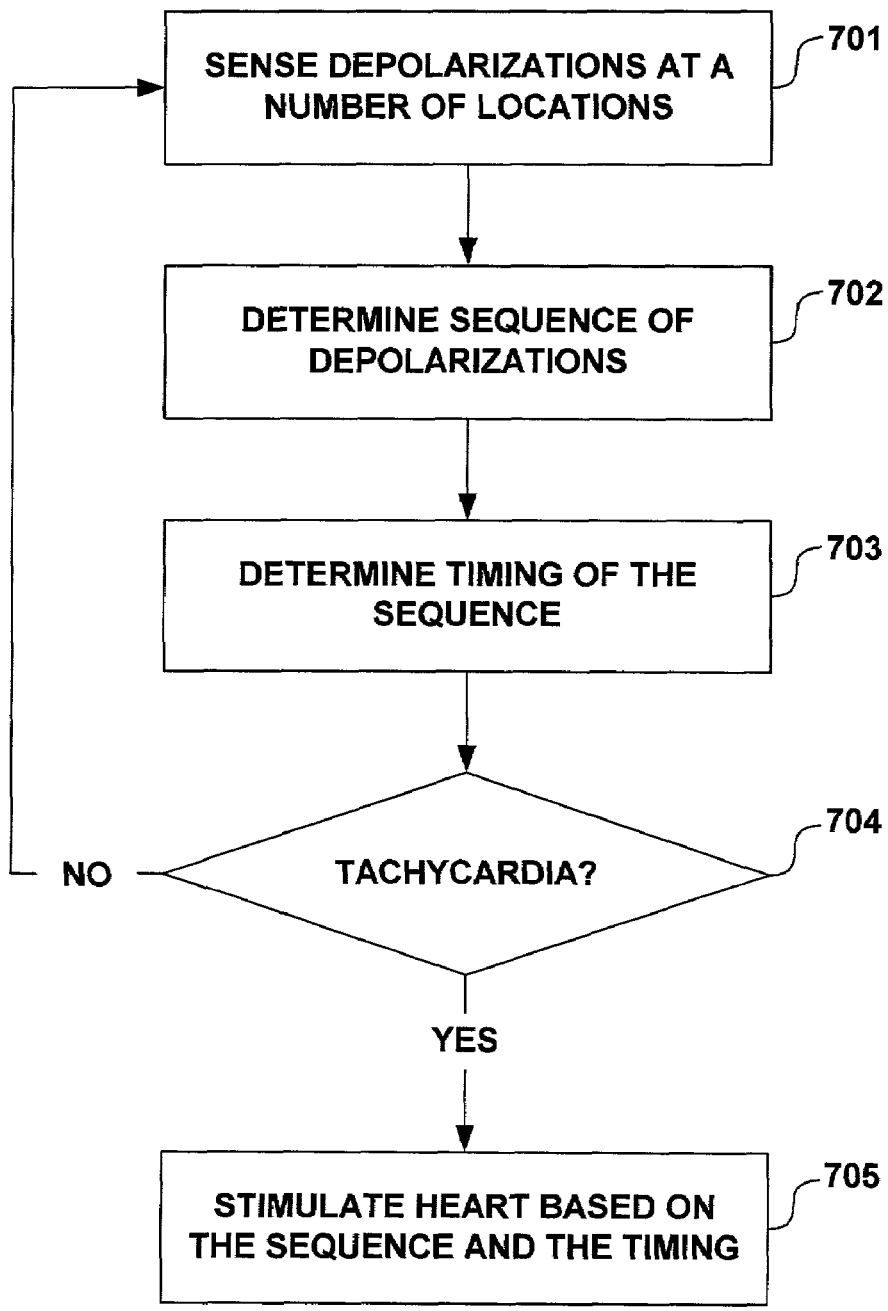
FIG. 7 is a flow diagram illustrating an anti-tachycardia technique according to one embodiment of the invention.

FIG. 7 is a flow diagram according to one embodiment of the invention. In particular, the flow diagram of FIG. 7 may correspond to a computer programmed algorithm programmed into pacemaker 10 as outlined above. In that case, for example, the algorithm can be stored in memory of pacemaker 10. Various components pacemaker 10 such as a microprocessor may execute the algorithm in order to perform anti-tachycardia pacing techniques according to the invention.

As shown, depolarizations are sensed at a number of locations (701) within the heart. For example, sense electrodes positioned at a number of locations around the heart may be used to sense the depolarizations. In some cases, the locations may be in different chambers of the heart, as well as at different locations within a particular heart chamber, such as the left ventricle. Having sensed the depolarizations, the pacemaker can then determine a sequence of the depolarizations (702) from location to location. For example, the pacemaker may include a control unit coupled to the electrodes that determines the sequence such as by storing an order of sensed depolarization as they occur. The control unit, for example, may include a microprocessor and memory coupled to the microprocessor similar to the configuration outlined above. In that case, the memory may store values associated with sensed depolarizations so that the microprocessor can determine the sequence. Importantly, the present invention not only senses the depolarizations, but also records the sequence associated with the depolarizations. Then, subsequent anti-tachycardia therapy can be delivered to the heart in a sequence that is the same as or similar to the sequence of sensed depolarizations. Accordingly, anti-tachycardia therapy can be defined according to the characteristics of the specific episode being measured.

In addition to determining the sequence of depolarizations (702), the pacemaker may also determine a timing of the sequence (703). In particular, the pacemaker can determine the time offset between successive depolarizations at the different locations. The sequence and timing can collectively define a map of the tachycardia that is both spatial in terms of the progression of the tachycardia depolarization between locations in the heart, and temporal in terms of the timing of the progression.

Optionally, the time offset between successive depolarizations at any given site may be measured in order to estimate the period of the tachycardia. In some embodiments, the period can be estimated by measuring the time offset between successive depolarizations at one site defined by the placement of a particular electrode. In other embodiments, the period may be estimated by measuring the time offset between successive depolarizations at a number of different sites or all of the sites associated with electrodes. In any case, the period of the tachycardia can be used to define an optimal window of time offset after depolarization in any given local, when an anti-tachycardia stimulus can be effectively delivered. In other words, the determined period can be used to define repolarization intervals for the respective locations during which effective delivery of anti-tachycardia stimuli can be employed. Thus, in some embodiments, stimuli are provided according to a detected sequence, a timing of the sequence, and a period associated with the tachycardia.

The determined period may be used to assess whether a tachycardia condition is present (704). In other words, the determined period may be compared to a period associated with normal sinus rhythm in order to determine whether depolarizations are occurring at a rate that is too fast or too slow. Alternative or additional techniques, such as pressure sensing techniques and the like, may also be employed to identify a tachycardia condition prior to stimulating the heart according to the determined sequence of depolarizations.

If tachycardia is detected (704), the heart can be stimulated based on the determined sequence and the timing of the sequence (705). In other words, delivery of stimuli to the heart at the various locations defined by the various electrodes can be employed in a timed sequence that is substantially the same as or similar to the detected timed sequence of depolarizations. The delivery sequence may be an ordered sequence, wherein the order is the same as an order of detected depolarizations. Also, the delivery sequence may be a timed delivery sequence, with the timing between successive stimuli provided at different locations being defined by the detected timing of the sequence of detected depolarizations. Optionally, the detected period can be used to define the optimal time for delivery of the stimuli at each location.

In short, the sequence and timing of depolarizations can define the timed delivery sequence of stimuli, and the period of the tachycardia can be used in conjunction with the timed delivery sequence to define repolarization intervals for the respective locations. In this manner, anti-tachycardia pacing techniques can be improved to more quickly and reliably terminate a specific tachycardia episode because the timed delivery sequence of therapeutic stimuli are defined specifically for the episode. Thus, the invention can improve the potential effectiveness of anti-tachycardia therapy delivered by an implantable device. In other words, the delivery of multiple stimuli according to the determined sequence can create multiple refractory zones around the heart, which can end the tachycardia episode.

Figure 8:
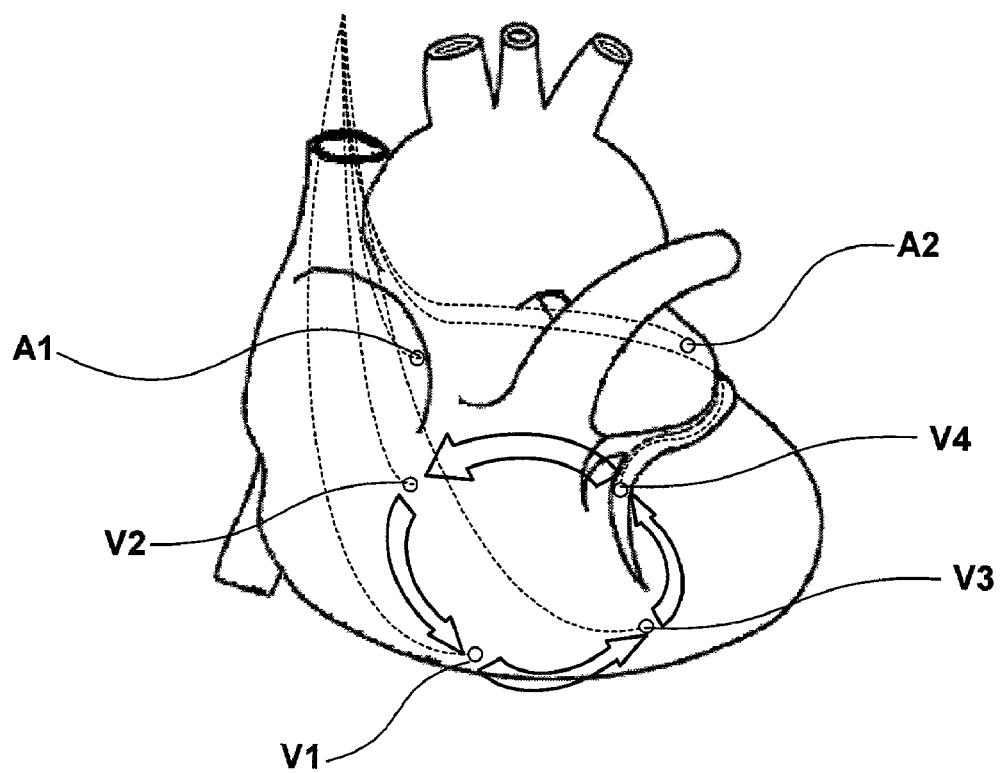
FIG. 8 is another schematic view of a heart and electrodes of an implantable medical device used to provide multi-site anti-tachycardia pacing therapy to the heart.

FIG. 8 is another schematic view of a heart and electrodes of an implantable medical device used to provide anti-tachycardia therapy to the heart. As mentioned above, the invention may be implemented with any number of leads and any number of electrodes in a multi-site pacing setting. In the example of FIG. 8, two electrode pairs are positioned to sense and pace the atria (A1 and A2), and four electrode pairs are positioned to sense and pace the ventricles (V1, V2, V3, V4). Each of these electrode pairs may be coupled to a pacemaker such as by leads (indicated by the dotted lines). The pacemaker can receive signals from the electrodes indicative of the occurrence of depolarization in the respective local. Then, after receiving signals from a number of the electrodes, the pacemaker can determine a sequence of the depolarizations, and if a tachycardia condition is present, may cause therapeutic stimuli to be delivered by the electrodes in a delivery sequence that is the same as or similar to the sequence of detected depolarizations. The timing of the sequence can also be measured so that the delivery sequence can be timed in the same as or similar manner.

Figure 9:
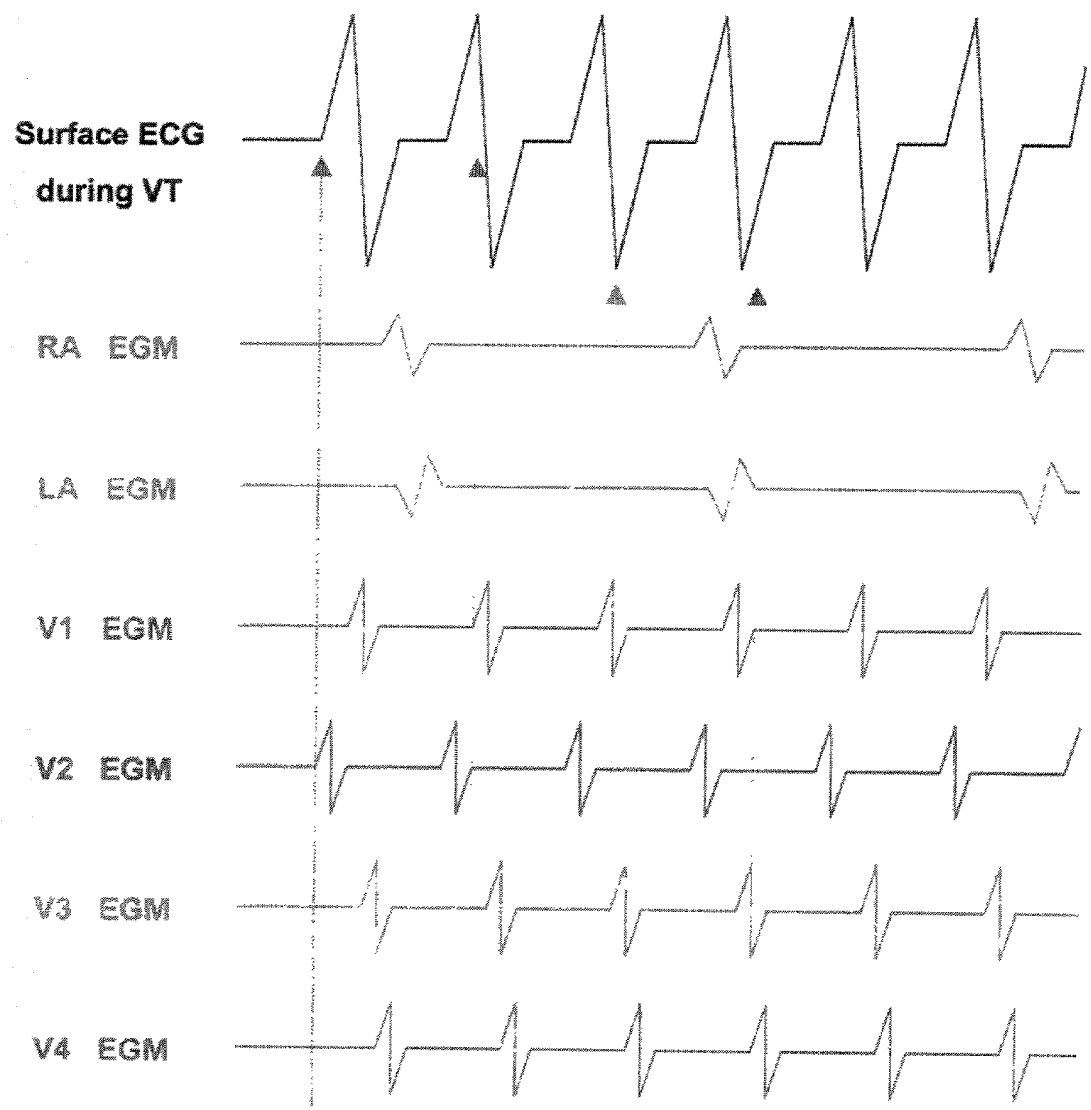
FIG. 9 is a timing diagram illustrating the detection of a sequence and timing of depolarization signals received from multiple electrodes of a multi-site pacemaker.

FIG. 9 is an exemplary timing diagram of various electrograms (EGMs) associated with the heart depicted in FIG. 8 during an episode of ventricular tachycardia. As illustrated in FIG. 9, the EGMs associated with the right atrium (RA) and left atrium (LA) have a much larger period than the EGMs associated with the ventricles. These or similar EGMs may be indicative of a condition of ventricular tachycardia in which the ventricles are contracting at a relatively high undesirable rate. In that case, in accordance with the invention, it may be desirable to provide therapeutic stimuli specifically to the ventricles and not to the atria. Thus, in accordance with the invention, the therapeutic stimuli may be provided at one or more ventricle sites according the detected sequence of depolarizations and the timing of the sequence at those locations. In other words, a stimulus can be provided to the location associated with the earliest onset of depolarization, followed by the location associated with the next onset of depolarization, followed by the next, and so forth. Each stimulus can be delivered in a timed manner, wherein the timed delivery sequence is similar to the timed sequence of depolarizations that are detected.

For example, as illustrated in FIG. 9, the depolarization begins in proximity to the pair of electrodes associated with V2 (FIG. 8). Next, the electrodes associated with V1 detect depolarization, followed by the electrodes associated with V3, and finally the electrodes associated with V4. By recording this sequence and the timing of the sequence, a mapping of the ventricular tachycardia can be realized. Accordingly, therapeutic anti-tachycardia stimuli can be provided at the ventricular electrodes according to the same as or similar sequence that the depolarizations were detected. Furthermore, if no tachycardia condition is detected in the atria, stimuli to the atria can be avoided. In this manner, a dynamically defined therapeutic stimuli sequence can be delivered according to the specific nature of the tachycardia episode.

Figure 10:
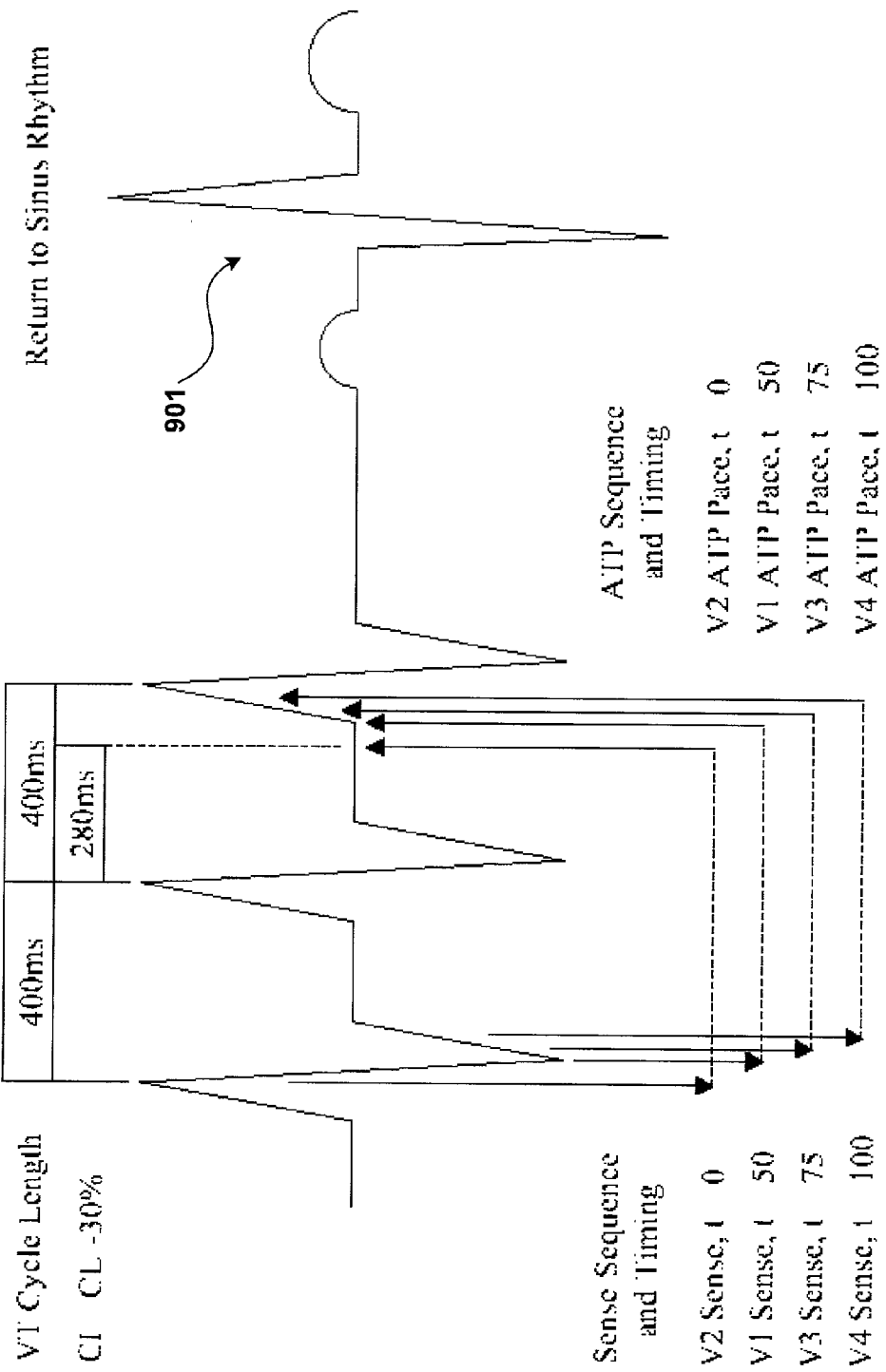
FIG. 10 is a timing diagram illustrating an anti-tachycardia pacing therapy that can be applied by an implantable medical device in response to detected signals illustrated in FIG. 8, according to an embodiment of the invention.

FIG. 10 is a timing diagram illustrating the delivery of therapeutic stimuli to the heart according to the sequence of depolarizations determined from the EGMs illustrated in FIG. 9. As shown, a pacing stimulus is provided at V2, then V1, then V3, and finally V4. In particular, each stimulus can be provided just before the detected depolarization at the given site. Thus, the delivery sequence may be substantially similar to the detected depolarization sequence. As illustrated, delivering a sequence of pacing stimuli in similar timed sequence that depolarizations were detected (FIG. 9) can enhance the likelihood of effectively returning the heart to normal sinus rhythm (as shown in surface ECG at numeral 901). The invention may also decrease the time is takes to end the tachycardia condition.

In particular, in the example illustrated in FIG. 10, the expected depolarization interval is the period between successive R-wave detections at a given site (the period of the tachycardia). Thus, the next intrinsic R-wave is expected to occur after the previous. For example, if the ventricular tachycardia has a period (cycle length) of 400 milliseconds (which corresponds to approximately 150 beats per minute), expected depolarizations at a given site will occur approximately every 400 milliseconds. In that case, the delivery of the ATP stimulus can occur at a time just before the next expected depolarization. In the example illustrated in FIG. 10, delivery of the ATP stimulus occurs at approximately (30%)*(cycle length) prior to the next expected depolarization. In other words the coupling interval is defined to be a percentage of the cycle length. The coupling interval can be fixed, or adjustable. For example, the coupling interval is typically between approximately 10% and 40% of the period of the tachycardia, although the invention is not limited in that respect.

Thus, as illustrated, the delivery of ATP stimuli are provided in the same sequence (V2, V1, V3, V4) as the detected sequence of depolarization, according to the same timing (V1 pace is 50 ms after V2, V3 pace is 75 ms after V2 and V4 pace is 100 ms after V2). Further, the pacing stimuli are provided during a window of time defined by the period. In other words, V2 pace is delivered 120 ms (30% of 400 ms) prior to the next expected depolarization. Thus, with a period of 400 ms, the pacing pulses are provided 280 ms after detected depolarizations. In other embodiments, the timing may differ. Importantly, however, the timed delivery sequence is defined by the detected sequence of depolarizations, the timing to the detected sequence, and the period of the tachycardia episode.

The amplitude and pulse width of the delivered stimuli may be defined to be slightly higher than the capture threshold programmed into the pacemaker. For example, amplitude and pulse width of the delivered stimuli may be programmed to have approximately 5 volt amplitude and a 0.5 ms pulse width, although the invention is not limited in that respect.

In various other embodiments, the stimuli may be provided to one heart chamber, if for example, only one heart chamber is experiencing tachycardia. In general, the invention can provide flexible and tachycardia-episode-specific therapy, according to the mapping of depolarizations for the specific episode. This can not only improve the effectiveness of ATP therapy, but can also avoid the delivery of stimuli to locations where the heart is not beating irregularly.

The physiological effect of delivering the ATP stimulus can yield a higher chance eliciting a premature capture of the local repolarized tissue. Thus, localized delivery of stimuli can promote capture of the tissue to block the re-entry of the ventricular tachycardia episode. In other words, the delivered ATP can gain access to the repolarized tissue, thus ending the tachycardia episode. The ATP stimulus can gain quick capture of newly repolarized tissue between the tail and the head of the circulating ventricular tachycardia episode, e.g., with a cycle length of approximately 400 ms. As the episode passes, it causes the initial depolarization, followed by repolarization again. Once this tissue is repolarized, during the early coupling interval, e.g., approximately 20–30% of the cycle length, a premature ATP stimulus can capture the local tissue and create a refractory block that can block the arriving ventricular tachycardia depolarization. Thus, as the ATP depolarization wavefront collides with the oncoming ventricular tachycardia wavefront, the tachycardia stops.

Figure 11:
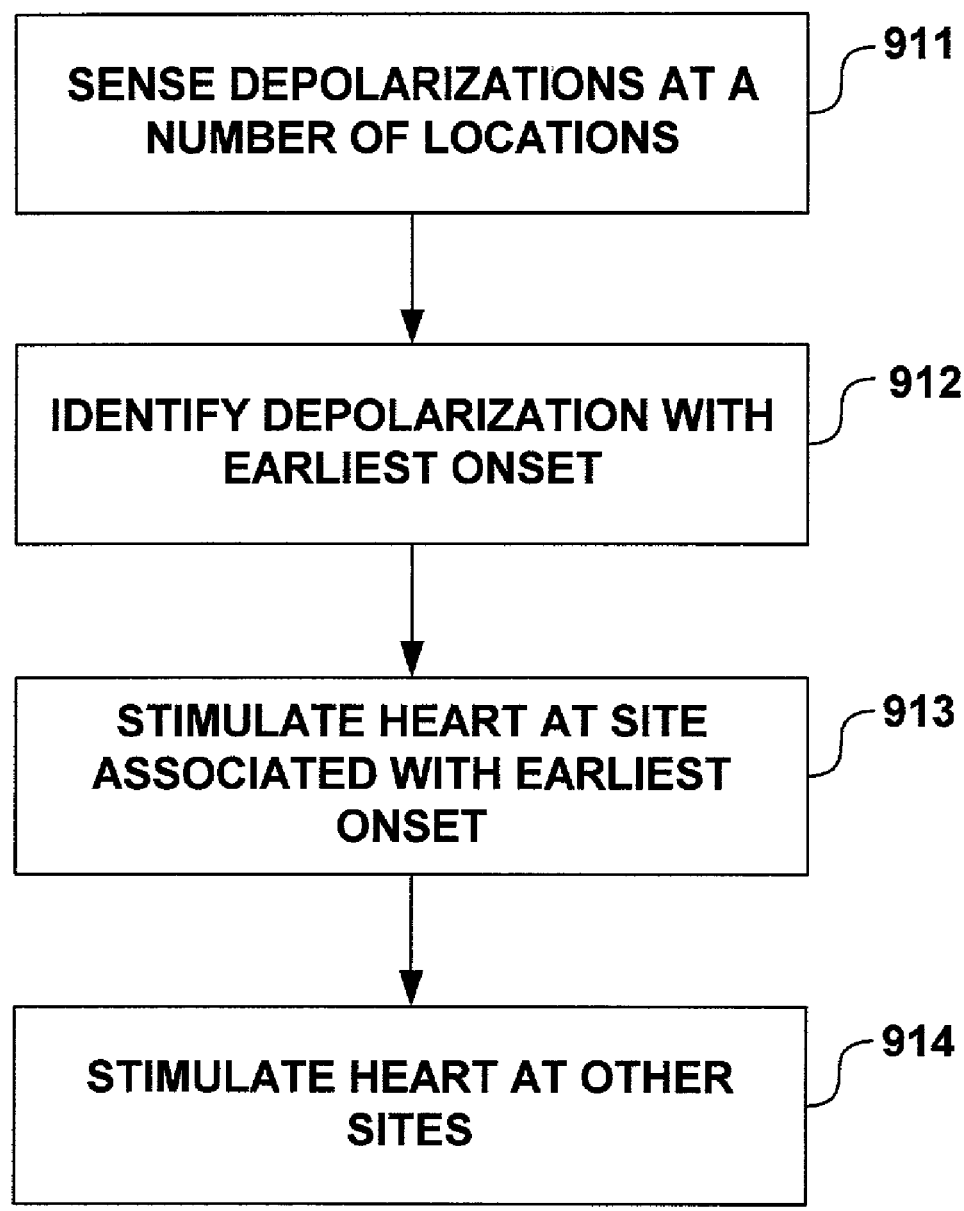
FIG. 11 is another flow diagram illustrating anti-tachycardia pacing techniques that can be employed within an implantable medical device.

FIG. 11 is another flow diagram illustrating anti-tachycardia pacing techniques that can be employed within an implantable medical device. As shown, electrodes of the implantable medical device sense depolarizations at a number of different locations (911). The depolarization having an earliest onset can then be identified (912), such as by identifying the first received signal after determining that a tachycardia condition is present. A control unit of the implantable medical device may then cause a stimulus to be provided specifically at the site associated with the earliest onset (913). In other words, a stimulus can be delivered at the site associated with the earliest onset of depolarization (913) prior to delivering a stimulus at other locals (914). In this manner, anti-tachycardia pacing therapy can be improved in a multi-lead implantable device setting.

Various embodiments of the invention may be embodied in methods, or implantable medical devices that carry out the methods. For example, a medical device may include a number of electrodes coupled to a control unit via implantable leads. In that case, the control unit may receive signals detected by the electrodes and cause the electrodes to deliver therapeutic stimuli in the manner outlined above. Moreover, the invention may be improved as more and more electrodes are employed. In other words, as more electrodes are employed, a more complete mapping of a tachycardia episode can be developed for the episode. Accordingly, as pacemakers become more and more complex, implementing more and more electrodes, the described invention can be improved by exploiting the additional electrodes to paint a more complete picture of each tachycardia episode, and deliver effective therapy accordingly.

In other embodiments, the invention may be directed to a computer readable medium comprising program code that causes an implantable medical device such as a pacemaker to carry out methods in accordance with the invention. In that case, the medium may store computer readable instructions, and the pacemaker may include a processor that executes the instructions in order to perform the methods. In still other embodiments, the invention may directed to a system within an implantable medical device. For example, the system may include memory that stores values indicative of sensed depolarizations of a heart at a number of different locations, and a processor coupled to the memory that generates a sequence of the sensed depolarizations.

The preceding specific embodiments are illustrative of the practice of the invention. It is to be understood, however, that in light of this disclosure, other embodiments will become apparent to those skilled in the art. For example some embodiments may be practiced in an external (non-implantable) or a partially external pacemaker device. Accordingly, these and other embodiments are within the scope of the following claims.

In the claims, means-plus-function clauses are intended to cover the structures described herein as performing the recited function and not only structural equivalents by also equivalent structures. Thus, although a nail and a screw may not be structural equivalents in that a nail employs a cylindrical surface to secure wooden parts together, whereas a screw employs a helical surface, in the environment of fastening wooden parts, a nail and a screw are equivalent structures.

The invention claimed is:

1. A method comprising: sensing depolarizations of a heart at a plurality of different locations within a single chamber of the heart; determining a sequence of the sensed depolarizations; and applying an anti-tachycardia stimulus to the heart at one or more of the locations based on the determined sequence further comprising determining a timing associated with the sequence, and applying an anti-tachycardia stimulus to the heart at one or more of the locations based on the timing of the sequence in an order defined by the sequence.

2. The method of claim 1, further comprising estimating a period associated with a tachycardia episode by sensing successive depolarizations for at least one of the locations and estimating the period based on a time offset between the successive depolarizations.

3. The method of claim 2, further comprising applying an anti-tachycardia stimulus to the heart at the locations based on the determined sequence, the timing of the sequence, and the estimated period.

4. The method of claim 3, wherein applying an anti-tachycardia stimulus to the heart at the locations based on the determined sequence, the timing of the sequence, and the determined period comprises: applying an anti-tachycardia stimulus to the heart at the locations in a timed delivery sequence defined by the determined sequence of sensed depolarizations and the timing of the determined sequence, wherein stimulus is delivered during windows of time defined by the period.

5. The method of claim 4, wherein the windows correspond to repolarization intervals for the respective locations.

6. The meThod of claim 1, further comprising identifying a tachycardia condition prior to applying the anti-tachycardia stimulus to the heart.

7. The method of claim 1, further comprising sensing the depolarizations of the heart at a plurality of different locations within one chamber of the heart.

8. The method of claim 1, further comprising sensing the depolarizations of the heart at a plurality of different locations within a plurality of different chambers of the heart.

9. The method of claim 1, further comprising storing the sequence.

10. A method comprising: sensing depolarizations of a heart at a plurality of different locations within a singele chamber of the heart; determining a sequence of the sensed depolarizations; determining a timing associated with the sequence; and upon identifying a tachycardia condition, stimulating the heart at the locations based on the sequence and the timing.

11. The method of claim 10, wherein the locations are ventricular locations.

12. A computer readable medium comprising program code that causes a pacemaker to: sense depolarizations of a heart at a plurality of different locations within a single chamber of the heart; determine a sequence of the sensed depolarizations; and apply an anti-tachycardia stimulus to the heart at the locations based on the determined sequence further comprising program code that causes a pacemaker to determine a timing associated with the sequence and apply an anti-tachycardia stimulus to the heart at the locations based the timing of the sequence in an order defined by the sequence.

13. The computer readable medium of claim 12, further comprising program code that causes a pacemaker to estimate a period associated with a tachycardia episode by sensing successive depolarizations for at least one of the locations and estimating the period based on a time offset between the successive depolarizations.

14. The computer readable medium of claim 13, further comprising program code that causes a pacemaker to stimulate the heart at the locations based on the determined sequence of sensed depolarizations, the timing of the sequence, and the estimated period.

15. The computer readable medium of claim 14, further comprising program code that causes a pacemaker to stimulate the heart at the number of locations based on the determined sequence of sensed depolarizations, the timing of the sequence, and the estimated period by: applying an anti-tachycardia stimulus to the heart at the locations according to a timed delivery sequence defined by the determined sequence of sensed depolarizations and the timing of the sequence, wherein the stimulus is delivered during windows of time defined by the period.

16. The computer readable medium of claim 15, wherein the windows correspond to repolarization intervals for the respective locations.

17. The computer readable medium of claim 12, further comprising program code that causes a pacemaker to detect a tachycardia condition prior to applying the anti-tachycardia stimulus to the heart at the locations.

18. The computer readable medium of claim 12, further comprising program code that causes a pacemaker to sense the plurality of depolarizations of the heart at a plurality of locations within one chamber of the heart.

19. The computer readable medium of claim 12, further comprising program code that causes a pacemaker to sense the plurality of depolarizations of the heart at a plurality of locations within a number of chambers of the heart.

20. The computer readable medium of claim 12, further comprising program code that causes a pacemaker to store the sequence.

21. A computer readable medium comprising program code that causes a pacemaker to: sense depolarizations of a heart at a plurality of different locations within a single chamber of the heart; determine a sequence of the sensed depolarizations; determine a timing of the sequence; and upon identifying a tachycardia condition, stimulate the heart at the number of locations based on the sequence and the timing.

22. The computer readable medium of claim 21, wherein the number of different locations are ventricular locations.

23. A system comprising: a memory that stores values indicative of sensed depolarizations of a heart associated with a plurality of different locations within a single chamber of the heart; and a processor coupled to the memory that generates a sequence of the sensed depolarizations and causes the heart to be stimulated at the plurality of locations based on the generated sequence wherein the processor generates a timing associated with the sequence and the processor causes the heart to be stimulated at the plurality of locations based on a timed delivery sequence defined by the generated sequence and the timing associated with the sequence.

24. The system of claim 23, wherein the memory stores values indicative of successive depolarizations for at least one of the locations and the processor estimates a period based on a time offset between the successive depolarizations.

25. The system of claim 24, wherein the processor causes the heart to be stimulated at the plurality of locations based on the generated sequence of the sensed depolarizations, the generated timing and the estimated period.

26. The system of claim 25, wherein the processor causes the heart to be stimulated by stimulating the heart at the plurality of locations in a timed delivery sequence defined by the generated sequence of the sensed depolarizations and generated timing, wherein stimulation occurs during windows defined by the estimated period.

27. The system of claim 26, wherein the windows correspond to repolarization intervals for the respective locations.

28. The system of claim 23, wherein the processor identifies a tachycardia condition prior to causing the heart to be stimulated at the plurality of locations based on the generated sequence.

29. The system of claim 23, wherein the memory stores values indicative of sensed depolarizations of the heart associated with a plurality of different locations within one chamber of the heart.

30. The system of claim 23, wherein the memory stores values indicative of sensed depolarizations of the heart associated with a plurality of different locations within a plurality of chambers of the heart.

31. The system of claim 23, wherein the memory stores the sequence.

32. A system comprising: a memory that stores values indicative of sensed depolarizations of a heart associated with a plurality of different locations within a single chamber of the heart; and a processor coupled to the memory that generates a sequence of the sensed depolarizations, generates a timing associated with the sequence, and upon identifying a tachycardia condition, causes the heart to be stimulated at the plurality of locations based on the sequence and the timing associated with the sequence.

33. The system of claim 32, wherein the plurality of different locations are ventricular locations.

34. An implantable medical device comprising: a plurality electrodes that sense depolarizations of a heart at a plurality of different locations within a single chamber of the heart; and a control unit coupled to the electrodes that determines a sequence of the sensed depolarizations and causes the electrodes to stimulate the heart at the plurality of different locations based on the determined sequence wherein the control unit determines a timing associated with the sequence and causes the electrodes to stimulate the heart at the plurality of different locations based on a timed delivery sequence defined by the determined sequence and determined timing.

35. The implantable medical device of claim 34, wherein at least one of the electrodes sense successive depolarizations for at least one of the locations, and the control unit estimates a period associated with a tachycardia episode based on a time offset between the successive depolarizations.

36. The implantable medical device of claim 35, wherein the control unit causes the electrodes to stimulate the heart at the plurality of locations based on the determined sequence of the sensed depolarizations, the determined timing, and the estimated period.

37. The implantable medical device of claim 36, wherein the control unit causes the electrodes to stimulate the heart at the plurality of locations by causing the electrodes to stimulate the heart at the plurality of locations according to a timed delivery sequence defined by the determined sequence of the sensed depolarizations and the determined timing, wherein stimulations are delivered during windows of time defined by the period.

38. The implantable medical device of claim 37, wherein the windows correspond to repolarization intervals for the respective locations.

39. The implantable medical device of claim 34, wherein the control unit identifies a tachycardia condition prior to causing the electrodes to stimulate the heart at the plurality of locations based on the determined sequence.

40. The implantable medical device of claim 34, wherein the electrodes sense the plurality of different depolarizations of the heart at a plurality of different locations within one chamber of the heart.

41. The implantable medical device of claim 34, wherein the electrodes sense the plurality of different depolarizations of the heart at a plurality of different locations within a plurality of chambers of the heart.

42. The implantable medical device of claim 34, wherein the control unit stores the sequence.

43. An implantable medical device comprising: a plurality electrodes that sense depolarizations of a heart at a plurality of different locations within a single chamber of the heart; and a control unit coupled to the electrodes that determines a sequence of the sensed depolarizations, determines a timing associated with the sequence, and upon identifying a tachycardia condition, causes the electrodes to stimulate the heart at the plurality of locations based on the sequence and the timing.

44. The implantable medical device of claim 43, wherein the plurality of different locations are ventricular locations.

45. An implantable medical device comprising: means for sensing depolarizations of a heart at a plurality of different locations within a single chamber of the heart; means for determining a sequence of the sensed depolarizations; and means for stimulating the heart at the plurality of locations based on the determined sequence means for determining a timing associated with the sequence and means for stimulating the heart at the plurality of locations based on a timed deliveiy sequence defined by the determined sequence and the determined timing.

46. The implantable medical device of claim 45, further comprising means for determining a period associated with a tachycardia episode and means for stimulating the heart at the plurality of locations based on the determined sequence, the determined timing and the determined period.

47. The implantable medical device of claim 45, further comprising means for identifying a tachycardia condition prior to stimulating the heart at the plurality of locations based on the determined sequence.

* * * * *

UNITED STATES PATENT AND TRADEMARK OFFICE
CERTIFICATE OF CORRECTION

PATENT NO. : 7,146,214 B2 Page 1 of 1
APPLICATION NO. : 10/126522
DATED : December 5, 2006
INVENTOR(S) : Struble It is certified that error appears in the above-identified patent and that said Letters Patent is hereby corrected as shown below:

Column 21, line 7 please change "stimul ate the heart" to --stimulate the heart--.

Column 22, line 17/18 please change "timed deliveiy" to --timed delivery--.

Signed and Sealed this

Twenty-third Day of October, 2007

JON W. DUDAS
*Director of the United States Patent and Trademark Office*